(12) United States Patent
Helland

(10) Patent No.: US 7,751,882 B1
(45) Date of Patent: Jul. 6, 2010

(54) METHOD AND SYSTEM FOR DETERMINING LEAD POSITION FOR OPTIMIZED CARDIAC RESYNCHRONIZATION THERAPY HEMODYNAMICS

(75) Inventor: John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 1133 days.

(21) Appl. No.: 11/316,254

(22) Filed: Dec. 21, 2005

(51) Int. Cl.
*A61N 1/00* (2006.01)
(52) U.S. Cl. .......................................................... 607/9
(58) Field of Classification Search ...................... 607/3, 607/9, 2, 14, 17–19, 27, 28, 39, 119, 126, 607/424; 600/124, 424
See application file for complete search history.

(56) References Cited

U.S. PATENT DOCUMENTS

| | | | |
|---|---|---|---|
| 5,738,096 A | 4/1998 | Ben-Haim | 128/653.1 |
| 6,066,094 A | 5/2000 | Ben-Haim | 600/437 |
| 6,285,898 B1 | 9/2001 | Ben-Haim | 600/374 |
| 6,438,408 B1 | 8/2002 | Mulligan et al. | 600/510 |
| 6,738,667 B2 | 5/2004 | Deno et al. | 607/23 |
| 6,751,492 B2 | 6/2004 | Ben-Haim | 600/374 |
| 6,795,732 B2 | 9/2004 | Stadler et al. | 607/17 |
| 6,923,772 B2 | 8/2005 | Yu et al. | 600/508 |
| 6,999,815 B2 * | 2/2006 | Ding et al. | 607/9 |
| 7,127,289 B2 | 10/2006 | Yu et al. | |
| 2002/0045809 A1 | 4/2002 | Ben-Haim | 600/374 |
| 2002/0045810 A1 | 4/2002 | Ben-Haim | 600/374 |
| 2002/0115939 A1 | 8/2002 | Mulligan et al. | 600/510 |
| 2003/0083702 A1 | 5/2003 | Stadler et al. | 607/14 |
| 2004/0127798 A1 | 7/2004 | Dala-Krishna et al. | 600/450 |
| 2004/0162497 A1 | 8/2004 | Bennett et al. | 600/513 |
| 2004/0176810 A1 | 9/2004 | Stadler et al. | 607/17 |
| 2005/0027323 A1 | 2/2005 | Mulligan et al. | 607/18 |
| 2005/0149138 A1 | 7/2005 | Min et al. | 607/27 |
| 2006/0009811 A1 * | 1/2006 | Sheldon et al. | 607/17 |
| 2006/0041298 A1 * | 2/2006 | Yu et al. | 607/122 |
| 2006/0190045 A1 * | 8/2006 | Marcus et al. | 607/17 |
| 2007/0027489 A1 * | 2/2007 | Gill et al. | 607/9 |
| 2007/0219591 A1 * | 9/2007 | Zdeblick et al. | 607/17 |
| 2008/0065164 A1 * | 3/2008 | Ben-Haim et al. | 607/9 |
| 2008/0269822 A1 * | 10/2008 | Ljungstrom et al. | 607/18 |
| 2009/0005675 A1 * | 1/2009 | Grunwald et al. | 600/424 |

FOREIGN PATENT DOCUMENTS

| | | |
|---|---|---|
| EP | 0 944 350 B1 | 7/1997 |
| WO | WO 97/24981 | 7/1997 |
| WO | WO 02/053228 A1 | 7/2002 |
| WO | WO 03/037177 A2 | 5/2003 |
| WO | WO 03/037428 A2 | 5/2003 |

\* cited by examiner

*Primary Examiner*—George Manuel
*Assistant Examiner*—Robert N Wieland

(57) ABSTRACT

An electro-mechanical activation probe obtains information pertaining to both myocardial electrical activity and myocardial mechanical activity at each of a plurality of locations relative to the myocardium of a heart chamber. For each location, the temporal difference between a feature of the electrical activity, such as the QRS complex of an IEGM, and a feature of the mechanical activity, such as the onset of myocardial contraction, is compared to obtain a mechanical activation delay. A stimulation electrode is then positioned at one of the locations based on the comparison. The electrode may be positioned at the location having the greatest mechanical activation delay. Other mechanical activity, such as contractual force, may be used in conjunction with the mechanical activation delay to determine the optimal electrode location.

20 Claims, 6 Drawing Sheets

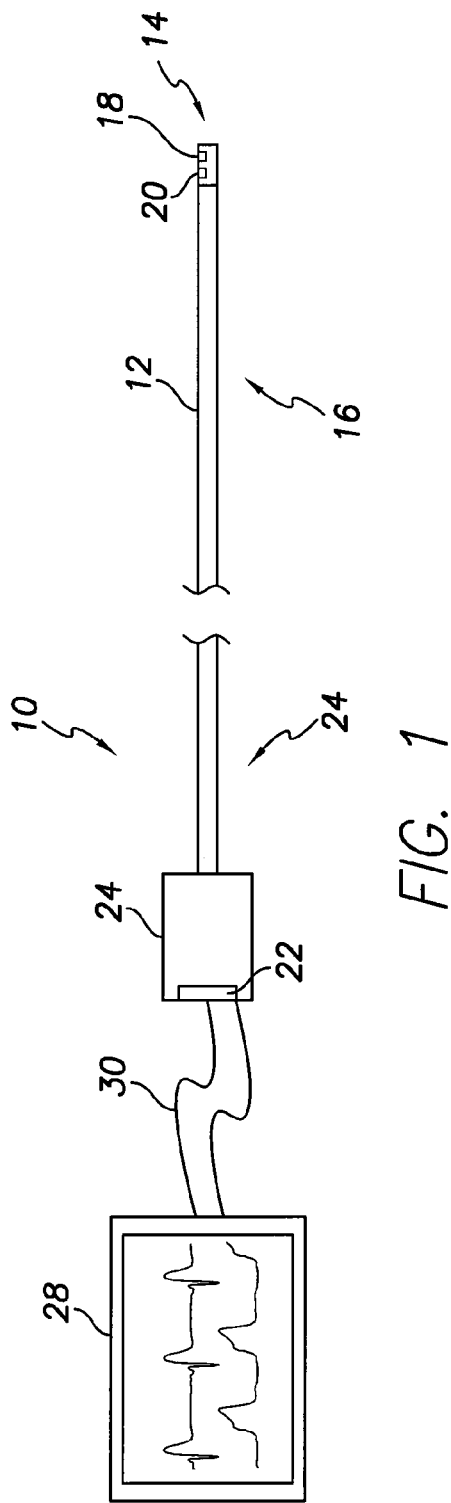
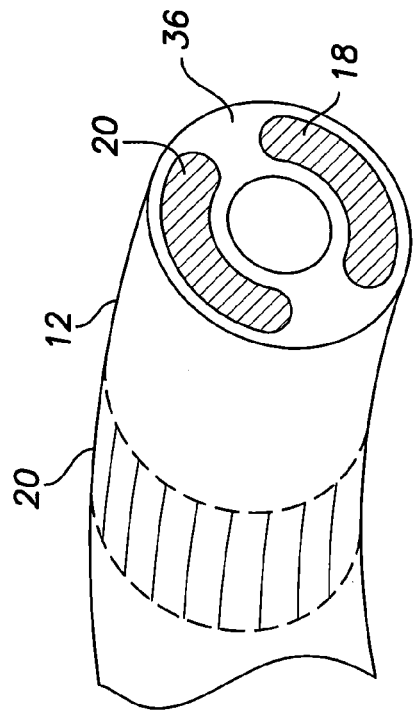
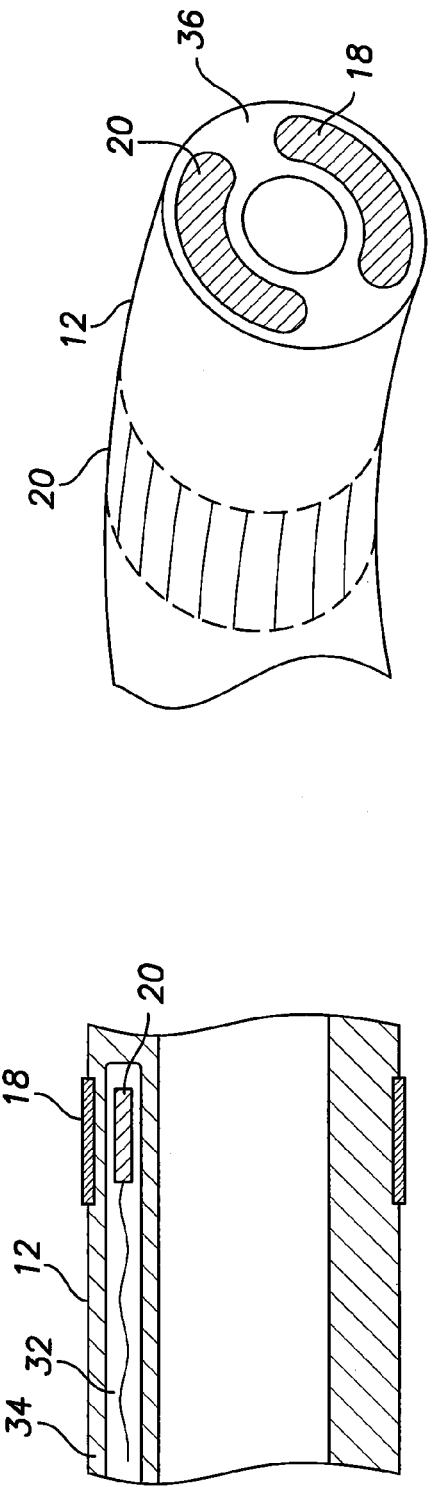
FIG. 1
FIG. 2a
FIG. 2b

METHOD AND SYSTEM FOR DETERMINING LEAD POSITION FOR OPTIMIZED CARDIAC RESYNCHRONIZATION THERAPY HEMODYNAMICS

FIELD OF THE INVENTION

The invention relates generally to implantable cardiac stimulation systems for use in pacing the heart and in particular to techniques for determining optimal positions for one or more electrodes for use primarily in heart failure patients.

BACKGROUND

Heart failure is one of the most widespread and devastating cardiac afflictions, currently affecting approximately 15 million people worldwide, including over 5 million in the United States. In the U.S., approximately 450,000 new patients are diagnosed with heart failure each year. One factor that contributes to heart failure is asynchronous activation of the ventricles such that the mechanical contraction is not coordinated effectively thus compromising cardiac function. As a result, the pumping ability of the heart is diminished and the patient experiences shortness of breath, fatigue, swelling, and other debilitating symptoms. The weakened heart is also susceptible to potentially lethal ventricular tachyarrhythmia. A decrease in cardiac function can result in a progression of heart failure. In many cases, pacing control parameters of the pacemaker or implantable cardioverter defibrillator (ICD) can be adjusted to help improve cardiac function and reduce the risk or degree of heart failure.

One particularly promising technique for reducing the risk of heart failure is cardiac resynchronization therapy (CRT). CRT seeks to normalize asynchronous cardiac electrical activation and the resultant asynchronous contractions by delivering synchronized pacing stimulus to both ventricles using pacemakers or implantable cardioverter defibrillators (ICDs) equipped with biventricular pacing capability. The stimulus is synchronized to help improve overall cardiac function. This may have the additional benefit of reducing the susceptibility to life-threatening tachyarrhythmias.

For example, within patients subject to left bundle branch block, pacing signals delivered to the left ventricle (LV) are timed relative to right ventricular pacing signals for the purpose of improving cardiac function. Briefly, within such patients, natural electrical signal nerve conduction pathways are damaged or blocked and so intrinsic pacing signals from the sinus node do not follow normal pathways through the left bundle branch and into the left ventricular myocardium to allow the LV to contract efficiently and uniformly. Instead, the electrical signals propagate through alternate pathways, particularly through the myocardium itself, resulting in different portions of the left ventricular myocardium contracting at different, less than appropriate or optimal times. Since the LV does not contract uniformly, its pumping efficacy is reduced and overall cardiac function is impaired.

With CRT, pacing pulses are delivered directly to the LV in an attempt to ensure that the left ventricular myocardium will contract more uniformly. A time delay relative to atrial pacing pulses and to right ventricular pacing pulses is set in an attempt to achieve optimal cardiac function. Typically, a right-ventricle left-ventricle (RV-LV) delay is initially set to zero while an atrioventricular (AV) delay (i.e. the pacing time delay between the atria and the ventricles) is adjusted to yield the best cardiac function. Then, the RV-LV delay is adjusted to achieve still further improvements in cardiac function. Within most patients, the RV-LV delay is set to a positive value, i.e. the LV is paced slightly before the right ventricle (RV). In other patients, the RV-LV delay is negative such that the RV is paced slightly before the LV. Similar techniques are also employed for patients whose nerve conduction pathways are corrupted due to right bundle branch block or due to other problems such as the development of scar tissue within the myocardium following a myocardial infarction.

With current state-of-the-art CRT techniques, the relative timing between left ventricular and right ventricular pacing pulses is adjusted in an attempt to improve cardiac function. Although such techniques are effective, it would be desirable to provide further improvements so as to achieve still greater benefits in cardiac function. In particular, whereas current CRT techniques are primarily directed to determining the optimal time delay between various pacing pulses, even greater potential improvement in overall cardiac function may be gained by also identifying the optimal pacing electrode locations for use in conjunction with CRT techniques.

Unfortunately, accurately determining that site can be a tedious and an often times lengthy effort with less than preferred results. Current approaches for trying to achieve optimized hemodynamics are quite varied and necessarily limited. Some physicians attempt to use electrocardiograms to identify an optimal site, by determining the LV site of the latest electrical delay. Some utilize arterial pressures to identify the best sites (which generally result in increased blood pressure). Others may use trans-esophageal echo (TEE) or tissue Doppler imaging (TDI) to try and find the site of last LV mechanical activation. More recently, some physicians are finding that a more precise method of finding the site of last LV mechanical activation may be to combine TDI and endocardial mapping technology. The last activated site within the LV is believed to be the optimal site for pacing because it corresponds to portions of the LV myocardium that would otherwise contract last in response to intrinsic pacing pulses and hence which most significantly contributes to uneven contraction of the chamber. By delivering pacing pulses directly at that location, adjacent portions of the myocardium can be caused to contract sooner, thus improving the uniformity of left ventricular contraction and thereby improving stroke volume from the LV and hence improving overall cardiac function.

SUMMARY

Briefly, and in general terms, the invention is directed to methods and systems for determining a location for delivering cardiac pacing pulses to the myocardium of a heart chamber. Temporal information pertaining to both myocardial electrical activity and myocardial mechanical activity at a plurality of locations relative to the myocardium of the heart chamber is obtained. For each location, the temporal difference between a feature of the electrical activity and a feature of the mechanical activity is compared. A stimulation electrode is then positioned at one of the locations based on the comparison.

In another aspect, the invention is related to an electrode placement system that includes an elongated body and a processor. The body has a first sensor for sensing electrical activity of myocardium and a second sensor for sensing mechanical activity of myocardium and is configured to transport a lead to a position relative to myocardium. The processor is responsive to signals from the first and second sensors and is configured to obtain information pertaining to myocardial electrical activity and myocardial mechanical activity using the signals from the sensors. The processor is also configured to present the information in a time-based, comparative manner.

In another aspect, the invention involves a method of positioning a pacing electrode of a lead relative to myocardium. An elongated body having a first sensor for sensing electrical activity of myocardium and a second sensor for sensing mechanical activity of myocardium is introduced near the myocardium. The first and second sensors are positioned at a location in contact with myocardium. A time difference between a feature of myocardial electrical activity and a feature of myocardial mechanical activity is determined using signals from the first and second sensors. The sensors are repositioned and another time difference is determined for at least one other location to obtain a plurality of time differences. A location for positioning a pacing electrode is selected based on the determined time differences and a pacing electrode of a lead is transported to the selected location using the elongated body.

These and other aspects and advantages of the invention will become apparent from the following detailed description and the accompanying drawings which illustrate by way of example the features of the invention.

BRIEF DESCRIPTION OF THE DRAWINGS

FIG. 1 is a schematic diagram of a lead placement system including an electro-mechanical activation probe, in accordance with the invention;

FIG. 2a is a cross section of the distal end of a lead placement system showing a configuration of an electro-mechanical activation probe;

FIG. 2b is a partial perspective view of the end of a lead placement system showing another configuration of an electro-mechanical activation probe;

DETAILED DESCRIPTION

Figure 3:
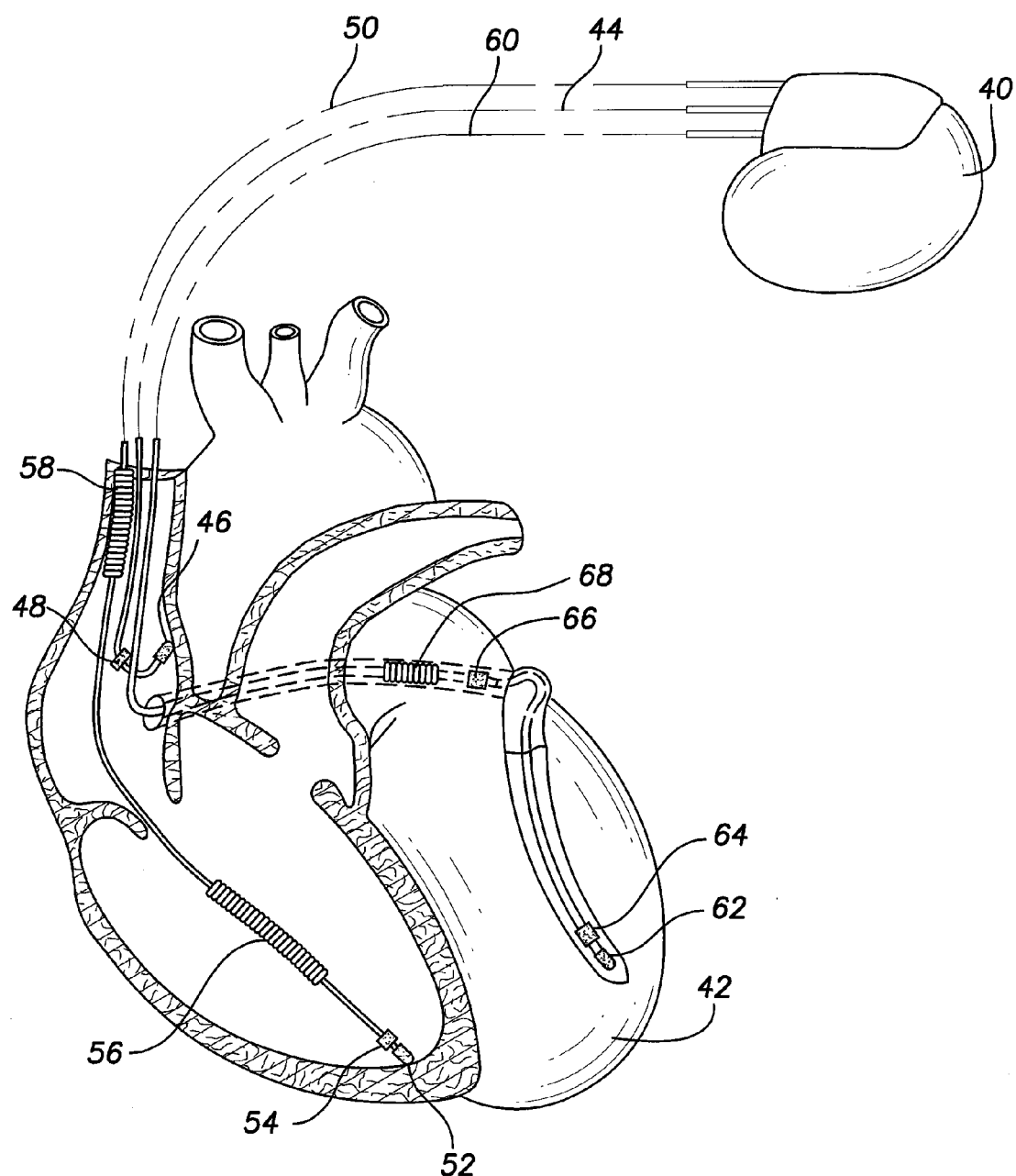
FIG. 3 is a simplified diagram illustrating an implantable cardiac stimulation device with at least three leads implanted in the heart of a patient for delivering multi-chamber stimulation and shock therapy.

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designations will be used to refer to like parts or elements throughout.

Referring now to the drawings and particularly to FIG. 1, there is shown a lead placement system 10 including an elongated body 12 with an electro-mechanical activation probe 14 at its distal region 16. The probe 14 includes an electrical sensor 18 and a mechanical sensor 20, each of which are electrically connected to a connector 22 included in a handle 24 at the proximal end 26 of the elongated body 12. The lead placement system 10 also includes a display device 28 that interfaces with the elongated body 12 through a cable 30 connected to the connector 22. The display device 28 records and displays the signals sensed by the electrical sensor 18 and the mechanical sensor 20.

The elongated body 12 may be a lead delivery tool or device that is used to place a cardiac lead in the heart transvenously, such as an introducer, guide catheter, guide sheath, guidewire or sheath, or on the heart epicardially, such as a lead implant tool as would be used for implanting. Alternatively, the elongated body 12 may itself be a lead. The electrical sensor 18 may be any one of several electrodes known in the art that are capable of sensing electrical activity in the heart, and in one configuration is a unipolar ring electrode. If the elongated body 12 is a lead, the electrical sensor 18 may be a distal tip electrode, a proximal ring electrode or any one of a plurality of electrodes on the lead. The mechanical sensor 20 may be a piezoelectric sensor, pressure sensor, accelerometer, magnetic ball or any other sensor known in the art that is capable of sensing mechanical activity, strain or pressure in the heart, such as that which may result from myocardial contraction.

The relative positions of the electrical sensor 18 and the mechanical sensor 20 are not critical, as long as they are positioned relatively close to each other along the axis of the elongated body 12. In one configuration, as shown in FIG. 1, the sensors 18, 20 are mounted on the exterior of the elongated body and are axially offset from each other. The sensors 18, 20 may be formed as discrete sensors positioned on the same side surface of the elongated body 12 or as ring sensors (not shown) surrounding the elongated body. Alternatively, as shown in FIG. 2a, the sensors 18, 20 may be generally axially aligned, with the electrical sensor 18 in the form of a ring electrode and the mechanical sensor inside a lumen 32 within the wall 34 of the elongated body 12. With reference to FIG. 2b, in other configurations, one or more sensors 18, 20 may be located at the end surface 36 of the elongated body 12. In one embodiment, one of the end-surface sensors is an electrical sensor 18 and the other is a mechanical sensor 20. In an alternate embodiment, both end-surface electrodes are electrical sensors 18 and the mechanical sensor 20 is a ring configuration.

With reference to FIG. 3, the lead placement system may be used during implant of a cardiac stimulation device 40 to determine the optimal locations of pacing electrodes, particularly those directed to the LV. By way of background, the stimulation device 40 may be a dual-chamber device that is capable of treating both fast and slow arrhythmias with stimulation therapy, including cardioversion, defibrillation, and pacing stimulation. Such devices are well known in the art and are described, for example, in U.S. Pat. No. 6,937,895, the disclosure of which is hereby incorporated by reference.

To provide atrial chamber pacing stimulation and sensing, the stimulation device 40 is in electrical communication with a heart 42 by way of a left atrial lead 44 having an atrial tip electrode 46 and an atrial ring electrode 48 implanted in the atrial appendage. The atrial ring electrode 48 allows for bipolar stimulation or sensing in combination with the atrial tip electrode 46. The stimulation device 40 is also in electrical communication with the heart by way of a right ventricular lead 50 having, in this embodiment, a ventricular tip electrode 52, a right ventricular ring electrode 54, a right ventricular coil electrode 56, and a SVC coil electrode 58. Typically, the right ventricular lead 50 is transvenously inserted into the heart so as to place the RV coil electrode 56 in the right ventricular apex, and the SVC coil electrode 58 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, the stimulation device 40 is coupled to a "coronary sinus" lead 60 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 60 is designed to receive atrial and ventricular cardiac signals and to deliver left ventricular therapy including: left ventricular unipolar pacing using at least a left ventricular tip electrode 62, left ventricular bipolar pacing using the left ventricular tip electrode 62 and a left ventricular ring electrode 64. The coronary sinus lead is further designed to deliver left atrial pacing therapy using at least a left atrial ring electrode 66, and shocking therapy using at least a left atrial coil electrode 68. With this configuration, biventricular pacing can be performed.

In alternate configurations of the coronary sinus lead 60, one of multiple ring electrodes functions as the left ventricular tip electrode 62 while another of the ring electrodes functions as the left ventricular ring electrode 64. In another configuration of the stimulation device 40, the left ventricular electrodes may be part of an epicardial lead such as that described in U.S. patent application Ser. No. 11/121,881, titled "Passive Fixation Mechanism for Epicardial Sensing and Stimulation Lead Placed Through Pericardial Access," the disclosure of which is incorporated by reference.

Figure 4:
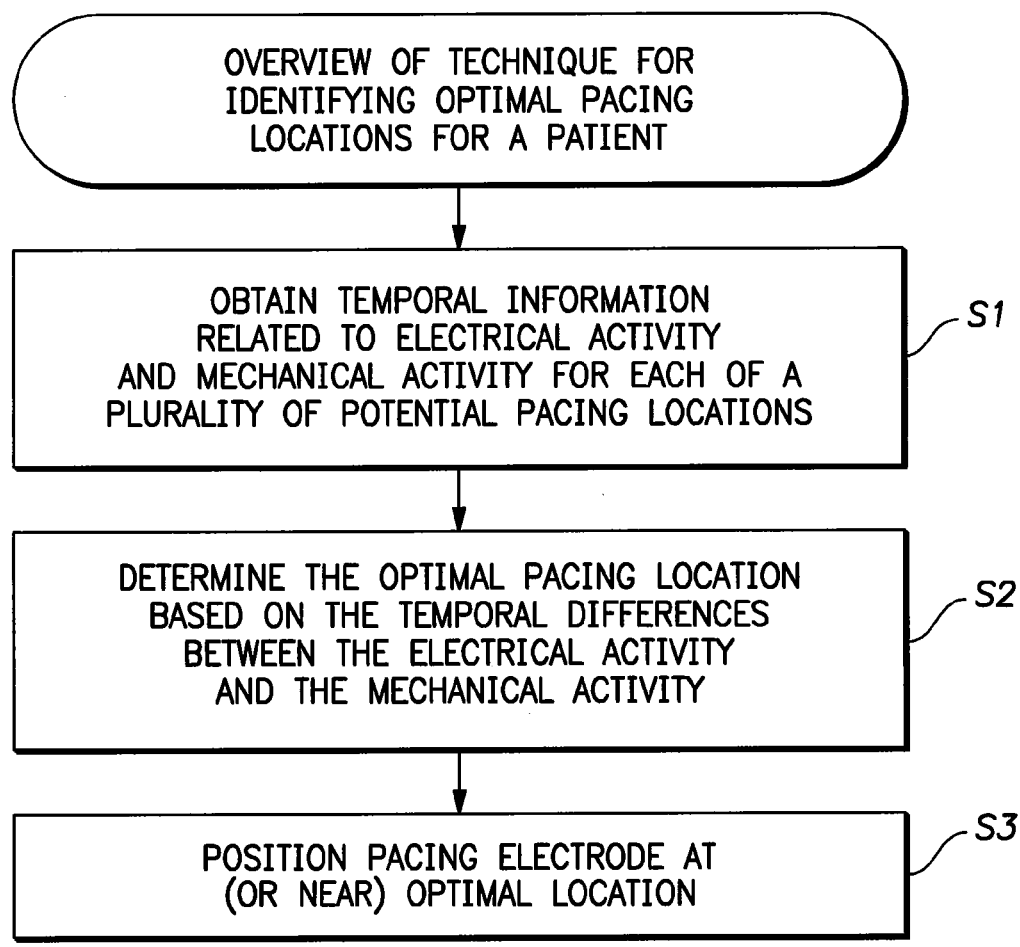
FIG. 4 is a flow chart of a general technique for identifying optimal locations for pacing electrodes based on differences between electrical cardiac activity and mechanical cardiac activity.

FIG. 4 provides an overview of a technique for identifying optimal or preferred pacing-electrode locations within the heart of a particular patient. Briefly, at step S1, temporal information related to both electrical activity and mechanical activity for a plurality of potential pacing locations for a heart chamber is obtained. Then, at step S2, the optimal pacing location for that chamber is determined based upon the temporal differences between the electrical activity and mechanical activity. Preferably, the location having the greatest delay between a particular feature associated with the electrical activity and a particular feature associated with the mechanical activity is identified as being the optimal or preferred pacing location. This delay is referred to as the "mechanical activation delay." For example, the location within the left ventricular myocardium having the greatest delay between the onset of a QRS complex and the onset of mechanical contraction may represent the optimal pacing location within the LV.

At step S3, a lead is implanted such that a pacing electrode associated with the lead is positioned at or near the optimal location for use in delivering pacing therapy. In an alternate technique, contractual force information related to mechanical activation at the locations is also obtained and used in conjunction with temporal information to determine the optimal pacing location. For example, the location having the greatest contractual force at the greatest mechanical activation delay may be selected as the optimal location.

Figure 5:
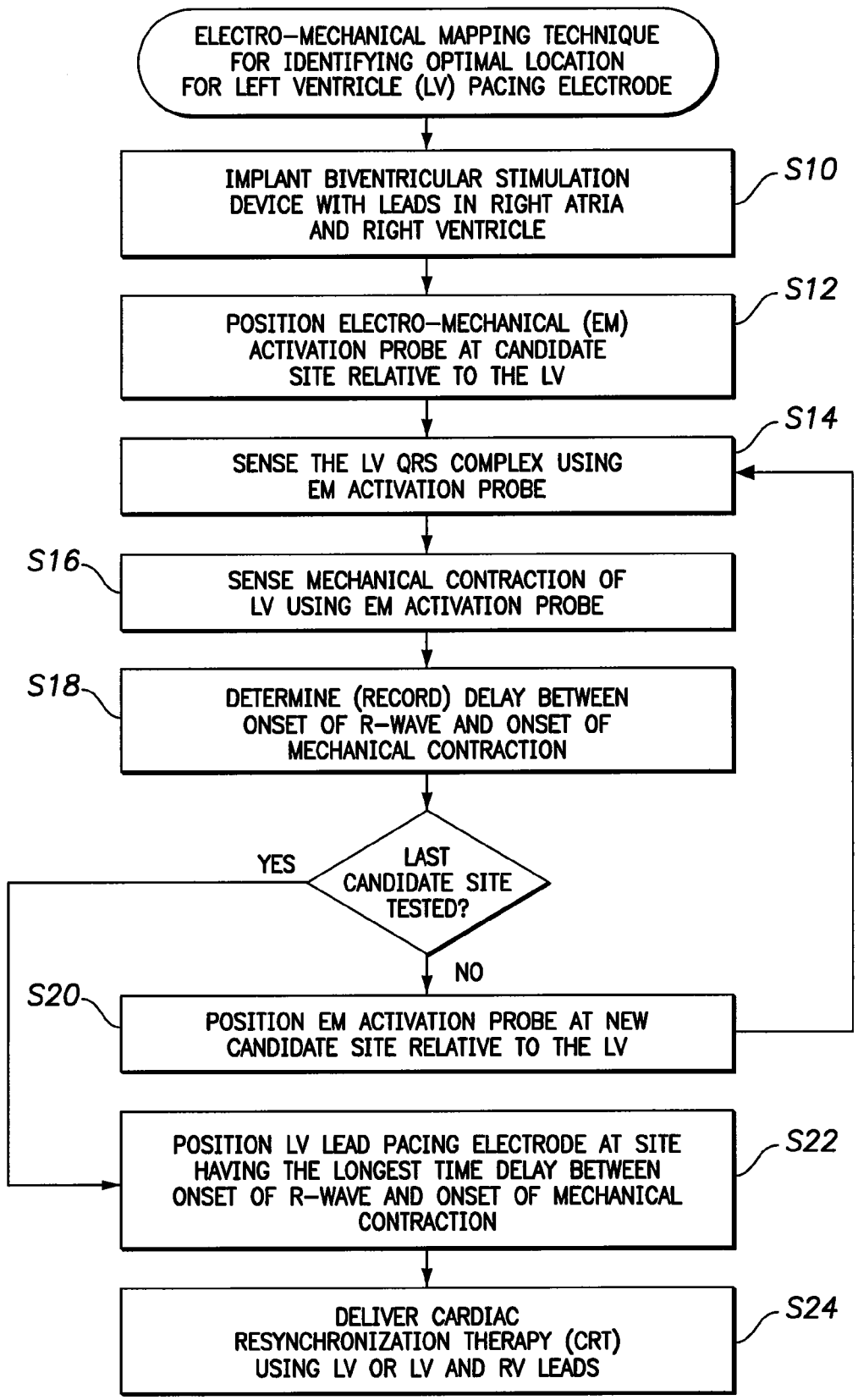
FIG. 5 is a flow chart of a technique for identifying an optimal location for a pacing electrode in the LV based on temporal differences between the QRS complex from the LV and the onset of mechanical contraction of the LV.

FIG. 5 illustrates an exemplary electrical-mechanical mapping technique for identifying the optimal location for placing the left ventricular tip electrode 62 (FIG. 3). Beginning at step S10, a biventricular pacemaker is implanted within the patient with leads 44 and 50 mounted within the atria and in the right ventricle (RV). At step S12, depending on the type of LV lead (endocardial or epicardial), an electro-mechanical activation probe 14 (FIG. 1) of a lead placement system 10 is positioned at a candidate location relative to the left ventricular myocardium. For example, in the case of an endocardial lead, the activation probe 14 may be positioned within a coronary vein overlying the LV. For epicardial leads, the activation probe 14 may be placed upon either the epicardial surface or the pericardial sac surface of the LV. In either case, the activation probe is positioned such that the probe sensors 18, 20 are against the left ventricular endocardium or epicardium. Possible locations include the lateral, anterior, posterior, basel and apical regions of the LV. Note that infarcted sites are avoided since such sites are not likely to respond to pacing stimulation. Infarcted regions may be identified using conventional techniques.

At step S14, an electrical, ventricular event is sensed by the electrical sensor 18 of the lead placement system 10. The electrical, ventricular event may be either an intrinsic depolarization (i.e. R-wave) or a paced event (i.e. a V-pulse). At step S16, a mechanical, ventricular event is sensed by the mechanical sensor 20 of the lead placement system 10. The mechanical, ventricular event may be movement or contraction of the ventricular myocardium or pressure within the LV.

Figure 6A:
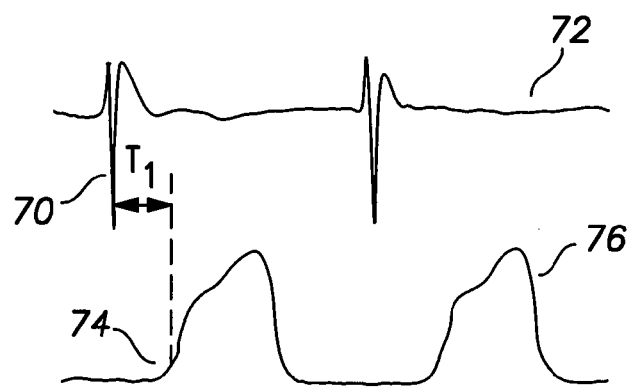
FIGS. 6a-6c are exemplary displays of IEGMs and mechanical contractions from the LV showing differences in the time delay between the R-wave and onset of mechanical contraction.

With reference to FIG. 6a, the time delay ($T_n$) between a particular feature of the electrical, ventricular event and a particular feature of the mechanical, ventricular event is determined at step S18 either by physician observation or possibly by a programmed processor. For example, the time delay between the peak of the R-wave 70 portion of the IEGM 72 and the onset 74 of the mechanical activation waveform 76 is observed and recorded by the implanting physician.

Figure 6B:
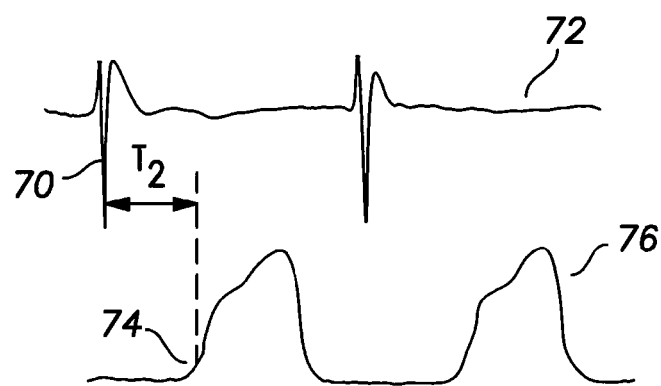
Figure 6C:
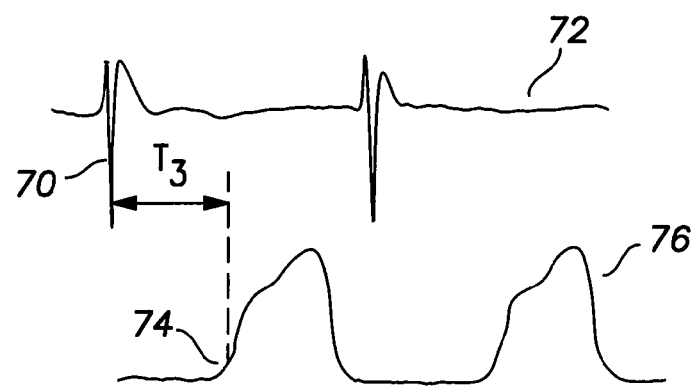

At step S20, the electro-mechanical activation probe is positioned at a new location and the process is repeated. Exemplary waveforms having varying time delays are shown in FIGS. 6b and 6c. Note that the IEGM and mechanical activity graphs provided herein are exemplary signals to illustrate features of the invention and should not be construed as being necessarily representative of clinical waveform data.

Once a time delay has been determined for each candidate location then, at step S22, the preferred or optimal location is determined based on a comparison of the various delays, with the site having the longest time delay selected as the optimal site. With reference to FIGS. 6a-6c, time delay $T_3$ in FIG. 6c is longer than time delays $T_1$ and $T_2$ in FIGS. 6a and 6b. Therefore, the site associated with the $T_3$ time delay would be selected as the optimal site. A contrast agent may be used to mark the optimal location for subsequent positioning of the left ventricular tip electrode 62. An endocardial sensing lead with capability for delivering a contrast agent is set forth in U.S. Pat. No. 6,377,856 to Carson, entitled "Device and Method for Implanting Medical Leads."

At step S24, the left ventricular tip electrode 62 is positioned at or near the optimal location. As previously described, the elongated body 12 of the lead placement system 10 may be configured as a device that is used to place a lead in the heart transvenously, such as an introducer, guide catheter, guidewire or sheath. It could also be a lead implant tool for use in placing a lead on the heart's epicardial surface via, for example, a mini-thoractomy. Alternatively, the elongated body 12 may itself be a lead. In the case where the lead placement system 10 includes an introducer, guide catheter or sheath, the tip electrode 62 is positioned at or near the optimal location by advancing the LV lead through the introducer, guide catheter or sheath to the location. If the lead placement system 10 includes a guidewire, the tip electrode is positioned by advancing the LV lead over the guidewire to the location. Beginning at step S26, once the tip electrode is placed at the optimal location, CRT (or other appropriate pacing therapy) is delivered using the stimulation device 40 via one or both of the left and right ventricular leads.

As noted, the determination of the optimal location performed at step S22 may be performed visually by the implanting physician. Alternatively, information related to the onset of the electrical and mechanical activity of the LV may be provided to an external programmer (or other external device). Conventional software programming techniques may be used to develop software for determining the time delay between appropriate features of the electrical, ventricular activity and mechanical, ventricular activity, for determining the optimal location from the various values, and for displaying the results on the external programmer for viewing by the physician or other medical personnel. Known graphics software may be employed for displaying a digital map or model of the heart of the patient along with an indication of the optimal pacing location so that the location can be easily visualized.

Figure 7A:
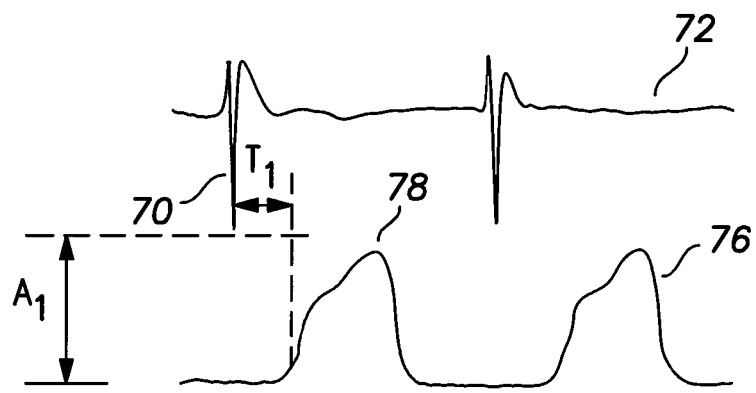
FIGS. 7a-7c are exemplary displays of IEGMs and mechanical contractions from the left ventricle showing differences in the amplitude of the mechanical contraction.
Figure 7B:
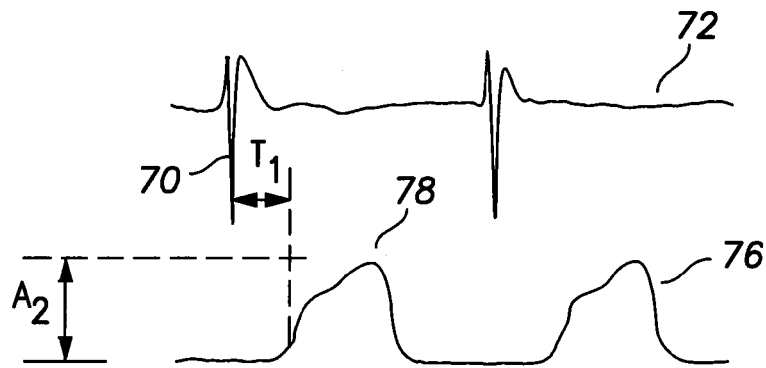
Figure 7C:
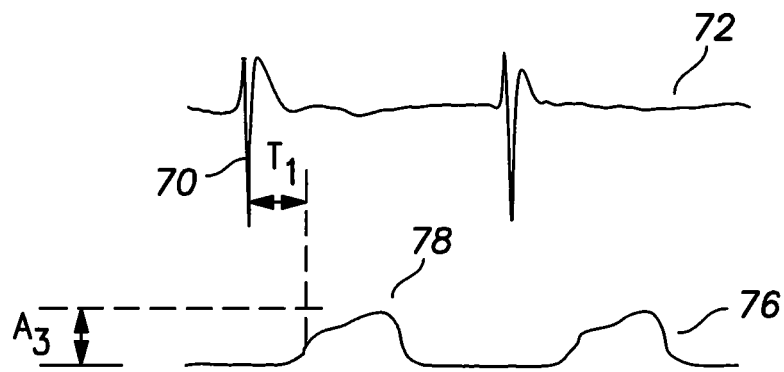

While the mechanical activity waveforms shown in each of FIGS. 6a-6c are offset in time with respect to each other, they are otherwise substantially the same. In practice, however, other characteristics of the mechanical waveforms may vary. For example, as shown in FIGS. 7a-7c, the peak amplitude 78 of the mechanical waveform 76 may be different at different myocardial sites. In accordance with another embodiment of the invention, additional characteristics of the mechanical waveform may be considered when selecting the optimal pacing site. For example, with reference to FIGS. 7a-7c, assuming the mechanical activation delay T between the relevant electrical activity feature, e.g., R wave, and the onset of mechanical activity of each are substantially the same, the site having the strongest contractual force, as indicated by the greatest mechanical activity of peak amplitude A, would be selected as the optimal pacing site. In FIGS. 7a-7c, the peak amplitude is at $A_1$.

In cases where a number of waveform features vary, the optimal site may be determined based on a synthesis of the waveform features. For example, if the various sites include both varying mechanical activation delay, such as shown in FIGS. 6a-6c and varying contractual forces, as shown in FIGS. 7a-7c, the site having the strongest contractual force at the greatest mechanical delay may be selected as the optimal site.

It will be apparent from the foregoing that while particular forms of the invention have been illustrated and described, various modifications can be made without departing from the spirit and scope of the invention. Consequently, the specific structural and functional details disclosed herein are merely representative and do not limit the scope of the invention. The scope of the invention should be ascertained with reference to the claims.

What is claimed is:

1. A method for determining a location for delivering cardiac pacing pulses to myocardium of a heart chamber, said method comprising:

using an electrical sensor and a mechanical sensor positionable relative to the myocardium of the heart chamber and a processor responsive to signals from the electrical sensor and the mechanical sensor to obtain temporal information pertaining to both myocardial electrical activity and myocardial mechanical activity at a plurality of locations relative to the myocardium of the heart chamber;

for each of the plurality of locations, comparing the temporal difference between a feature of the electrical activity and a feature of the mechanical activity; and positioning a stimulation electrode at the location having one of the largest temporal differences.

2. The method of claim 1 wherein the feature of the electrical activity comprises a feature of an intracardiac electrogram (IEGM).

3. The method of claim 2 wherein the feature of the IEGM is the QRS complex.

4. The method of claim 1 wherein the feature of the mechanical activity comprises the onset of the mechanical activity.

5. The method of claim 1 wherein the electrode is positioned at the location having the greatest temporal difference.

6. The method of claim 1 further comprising obtaining contractual force information pertaining to myocardial mechanical activity at the plurality of locations and wherein the electrode is positioned at the location having the greatest contractual force at the greatest temporal difference.

7. The method of claim 1 wherein obtaining temporal information comprises recording data indicative of myocardial electrical activity and myocardial mechanical activity.

8. The method of claim 1 wherein comparing the temporal information comprises presenting a time-aligned, visual display of myocardial electrical activity and myocardial mechanical activity.

9. An electrode placement system comprising:

an elongated body having a first sensor for sensing electrical activity of myocardium and a second sensor for sensing mechanical activity of myocardium, the body for transporting a pacing electrode to a position relative to myocardium; and a processor responsive to signals from the first and second sensors, and configured to:

obtain temporal information pertaining to both myocardial electrical activity and myocardial mechanical activity at a plurality of locations relative to the myocardium of the heart chamber;

for each of the plurality of locations, compare the temporal difference between a feature of the electrical activity and a feature of the mechanical activity; and identify the location having one of the largest temporal differences.

10. The system of claim 9 wherein the pacing electrode is part of a lead and the elongated body defines a lumen through which the lead may be transported.

11. The system of claim 9 wherein the pacing electrode is part of a lead and the elongated body defines a guidewire over which the lead may be transported.

12. The system of claim 9 wherein the pacing electrode and elongated body are part of a lead.

13. The system of claim 9 wherein the processor comprises a display for displaying images indicative of the obtained information.

14. The system of claim 9 further comprising a recorder for recording data indicative of the obtained information.

15. The system of claim 9 wherein the information pertaining to myocardial electrical activity is presented in the form of an intracardiac electrogram.

16. The system of claim 9 wherein the information pertaining to myocardial mechanical activity is presented as a function of time.

17. A method of positioning a pacing electrode of a lead relative to myocardium, said method comprising:
introducing an elongated body near myocardium, the body having a first sensor for sensing electrical activity of myocardium and a second sensor for sensing mechanical activity of myocardium;
positioning the first and second sensors at a location in contact with myocardium;
determining a time difference between a feature of myocardial electrical activity and a feature of myocardial mechanical activity using signals from the first and second sensors;
repeating the positioning and the determining steps for at least one other location to obtain a plurality of time differences;
selecting a location for positioning a pacing electrode, the location corresponding to the location having one of the largest time differences; and
transporting a pacing electrode of a lead to the selected location using the elongated body.

18. The method of claim 17 wherein the elongated body is introduced into a heart chamber.

19. The method of claim 17 wherein the elongated body is introduced into the pericardial space.

20. The method of claim 17 further comprising removing the elongated body from the area of the myocardium after transportation of the pacing electrode.

* * * * *